United States Patent [19]

Birum

[11] Patent Number: 5,052,054

[45] Date of Patent: Oct. 1, 1991

[54] CAP STRUCTURE WITH IMPLEMENT ADAPTER

[76] Inventor: Donald A. Birum, Rte. 1, Box 23, Clark, Mo. 65243

[21] Appl. No.: 459,467

[22] Filed: Jan. 2, 1990

[51] Int. Cl.[5] .............................................. A61F 9/00
[52] U.S. Cl. ...................................... 2/10; 2/185 B; 2/185 C; 2/185 R; 2/199; 2/422
[58] Field of Search .............. 2/10, 13, 185 B, 185 C, 2/185 R, 196, 199, 209.1, 209.2, 422

[56] References Cited

U.S. PATENT DOCUMENTS

| | | | |
|---|---|---|---|
| 1,171,155 | 2/1916 | Tannenbaum | 2/185 R |
| 1,586,701 | 6/1926 | Reppa | 2/196 |
| 1,611,771 | 12/1926 | Nathan | 2/185 C |
| 1,715,201 | 5/1929 | Levin | 2/185 C |
| 1,957,356 | 5/1934 | Rosen | 2/185 C |
| 2,578,112 | 12/1951 | Vaughn | 2/185 R |
| 2,704,367 | 3/1955 | Gellman | 2/199 |
| 2,803,016 | 8/1957 | Stevens | 2/185 B |
| 2,822,549 | 2/1958 | Glass | 2/185 R |
| 4,551,857 | 11/1985 | Galvin | 2/185 R |
| 4,764,989 | 8/1988 | Bourgeois | 2/422 |

FOREIGN PATENT DOCUMENTS 2754837  6/1979  Fed. Rep. of Germany ............ 2/10
818615  9/1937  France ................ 2/185 B Primary Examiner—Werner H. Schroeder
Assistant Examiner—Diana L. Biefeld

[57] ABSTRACT

A reinforcing structure for a soft cap (30) is provided as a thin cleat (96) positioned adjacent the flexible temple rim region (56) of the cap crown (32). The cleat is secured interior or exterior of the crown by various transferable or substantially permanent methods of attachment. A transferable securing arrangement includes a detachable clip (106) having a bight lip (108) for connecting with an edge of the cleat (96) and a U-shaped bight section (94) for engaging the crown temple rim (46). A portion of the clip body exterior of the crown may be adapted to support various utility implements including an eyewear (290) having adaptive temple members (202). An interior cleat may also function as a base for interior crown improvements including a crown shaping strip (100) or strips with curve adjacent the interior crown body and are adjustable for effective length. The shaping strip may additionally serve to retain a float disk (222) adjacent the interior crown (38). The float disk provides buoyancy to the cap and any attached implement should the cap be lost into a body of water.

39 Claims, 5 Drawing Sheets

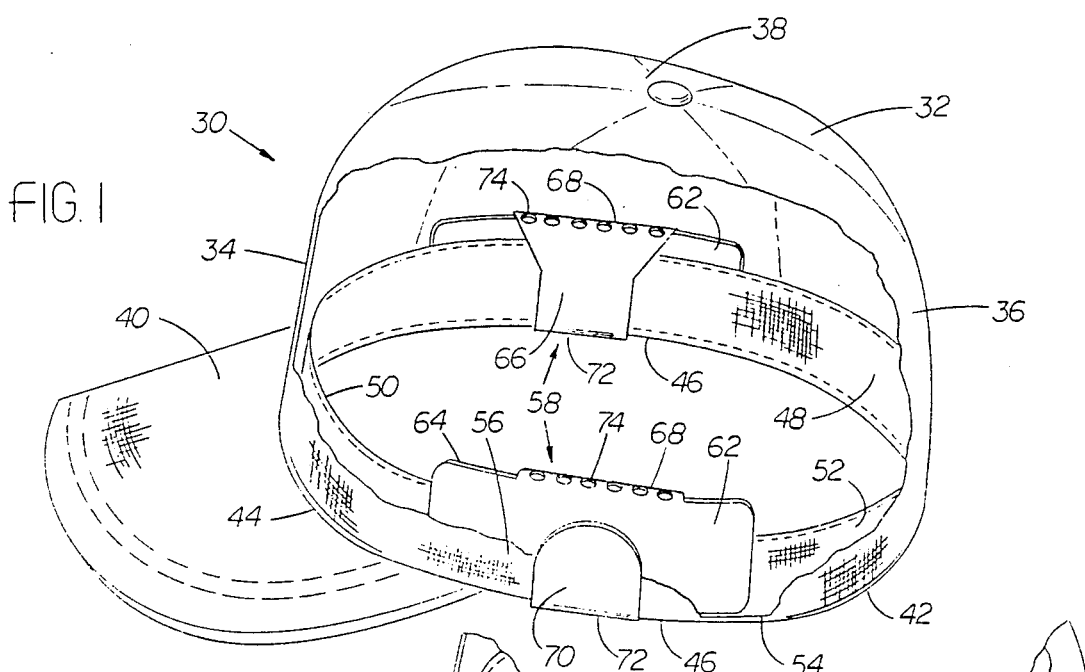
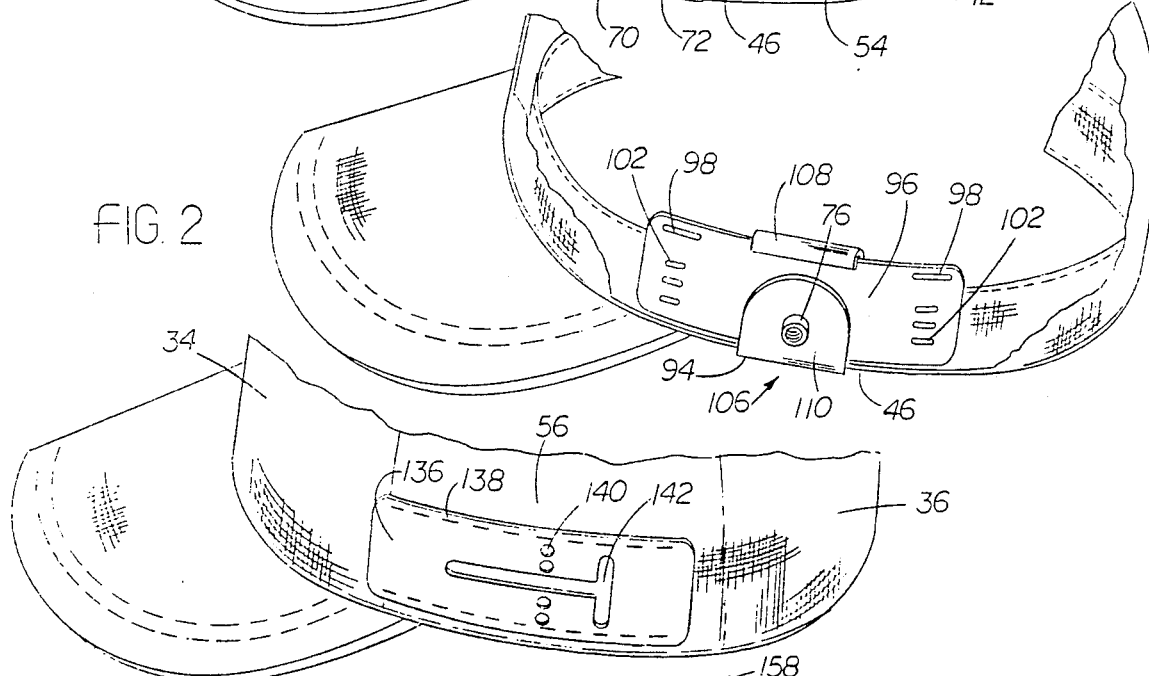
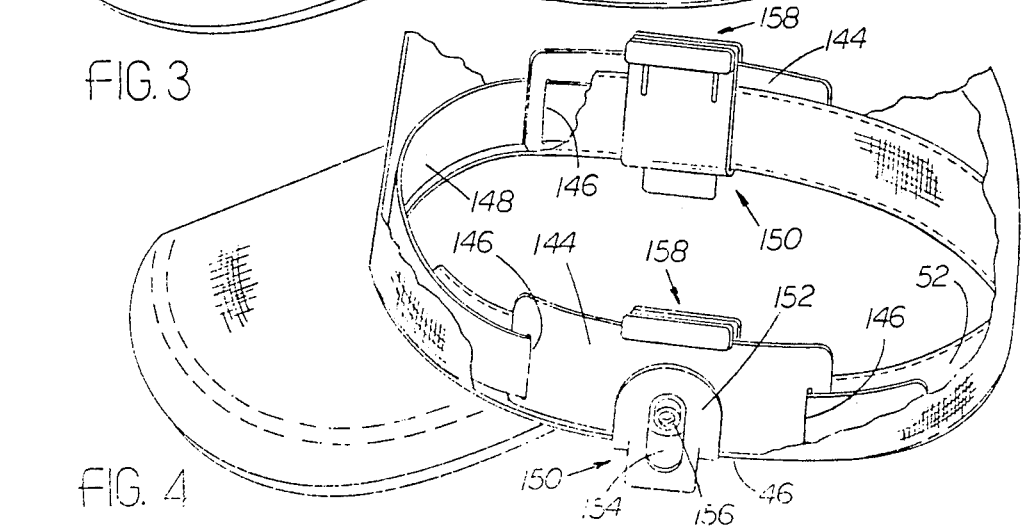

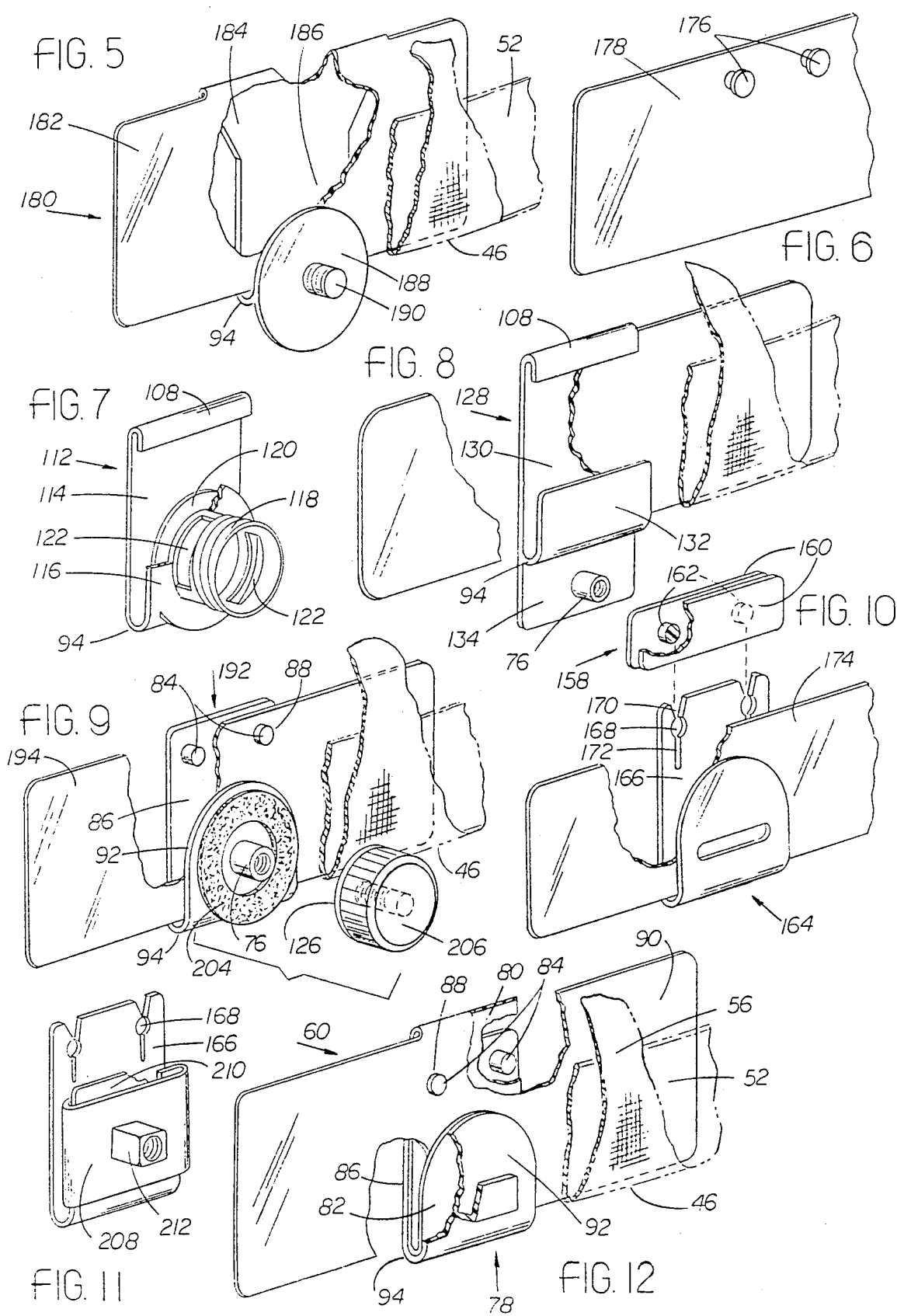

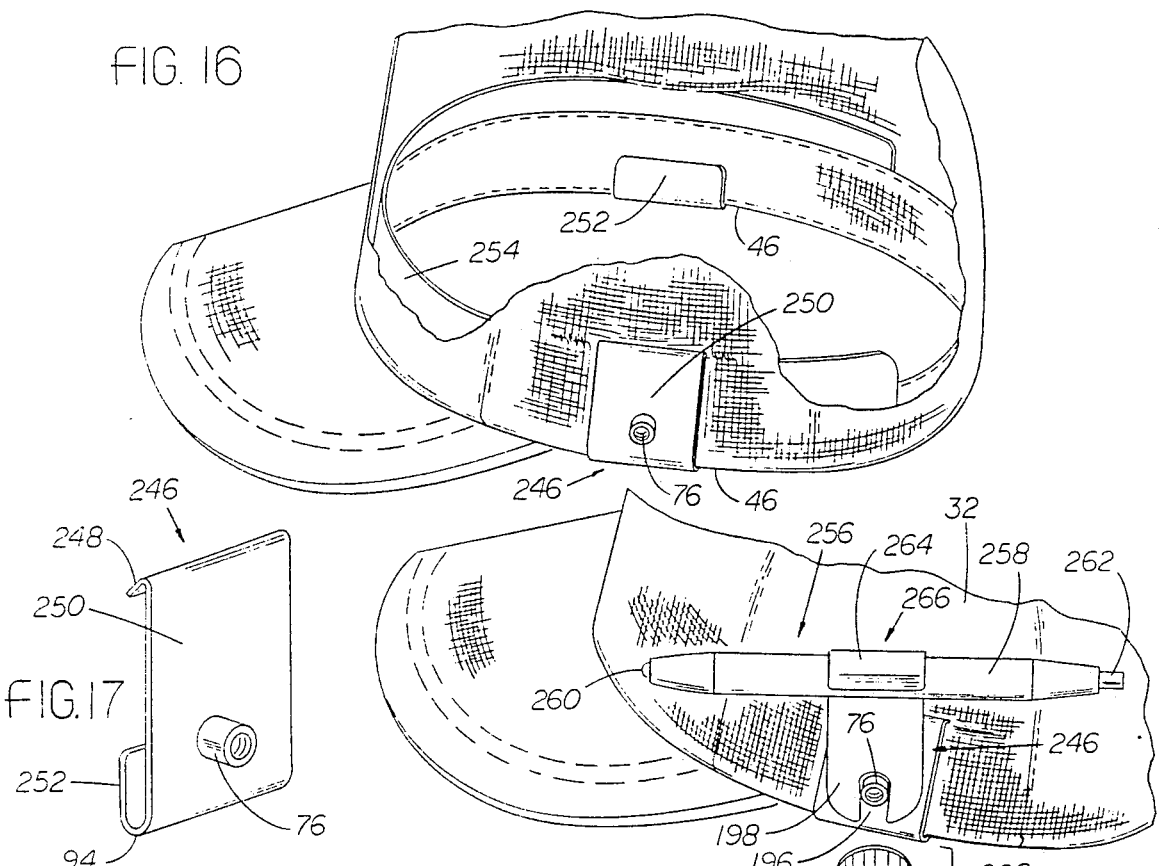
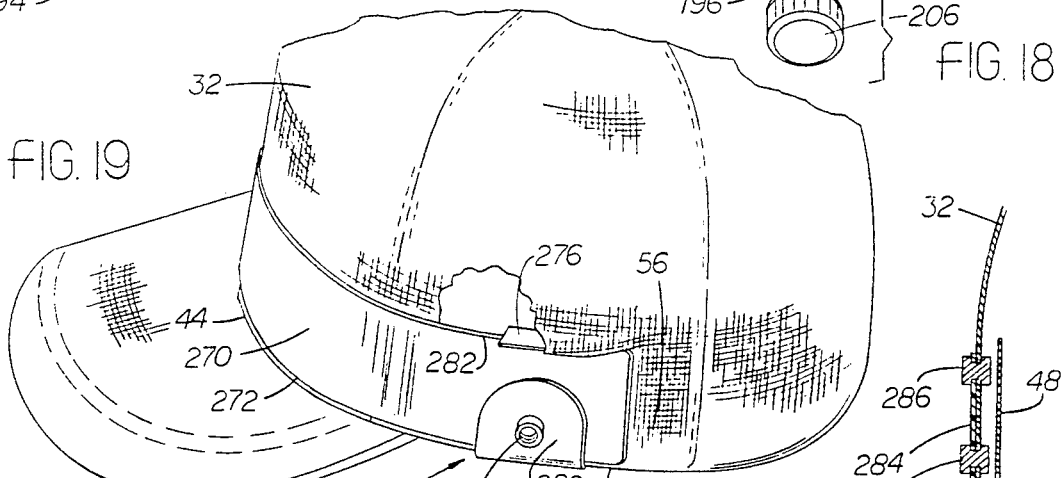
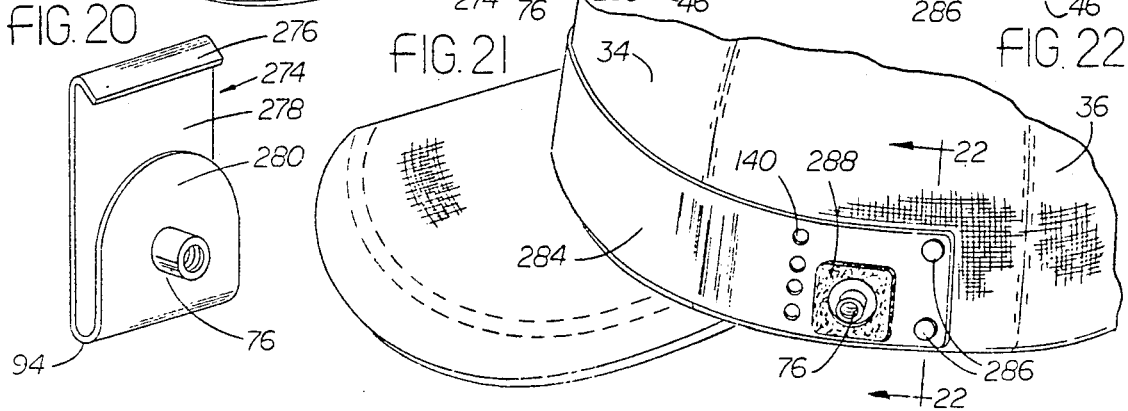

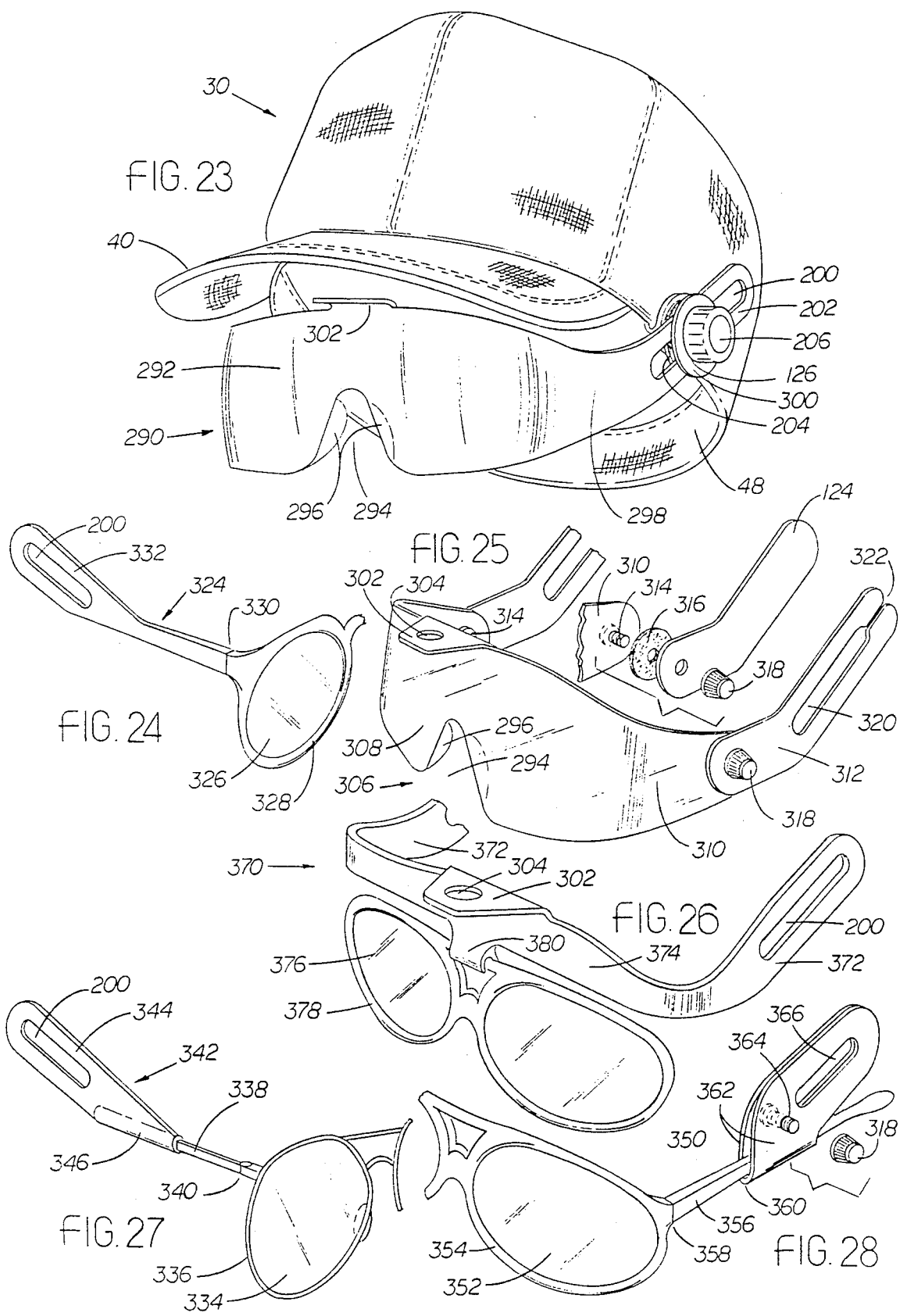

CAP STRUCTURE WITH IMPLEMENT ADAPTER

BACKGROUND-FIELD OF INVENTION

This invention relates to headwear, specifically to a structure for reinforcing the crown temple rim region of a soft cap, the structure being adaptable for interior cap improvements or exterior implement mounting.

BACKGROUND-DESCRIPTION OF THE PRIOR ART

Frontally billed baseball style soft caps are increasingly popular as headwear at work and for general outdoor and sport use. The elementary design of the cap has evolved for wearer comfort with a lightweight unstructured flexible crown and headband. The unstructured crown also allows a variety of materials and fabrics to be used in the cap manufacturing process and permits folding of the rear crown body into the frontal crown body for space saving in bulk packing or retail display.

Commonly however, the unstructured crown may lose form and aspect after moderate wear and washing, thus limiting the useful life of the cap. Only the reinforced bill may retain some original appearance. Accordingly, inventors have provided supplementary crown shaping devices for soft caps, the designs varying widely due to continuous changes in cap styles, materials and manufacturing techniques.

Examples of crown shaping devices for soft caps include U.S. Pat. No. 1,422,366 to Leger (1922), demonstrating a band formable into a closed ring and contoured to fit into the crown of a cap. U.S. Pat. No. 2,418,764 to Ford (1947), discloses a shaping structure utilizing a preassembled interior hemispherical frame of resilient strips. U.S. Pat. No. 2,697,835 to Stone (1954), reveals a contoured strip formable into a closed interior ring to support the specific shape of a military cap then in use. U.S. Pat. No. 4,858,247 to Hooser (1989), again demonstrates the use of a strip of material formable into a closed interior ring with the addition of a frontal extension.

While these devices relate utility as cap shaping structures in the configurations disclosed, they also demonstrate disadvantages associated with prior art in the field of cap shape retaining structures:

(a) The design will require additional manufacturing assembly time (Ford), or the design requires special tooling such as plastic molding apparatus for the primary shaping element (Hooser).

(b) The devices do not promote the use of adaptive staging or modes to enhance the utility of the structure (Leger, Ford, Stone).

(c) The devices limit applicability as to the style of cap which can be shaped.

(d) The devices are limited to an interior mounting to the cap.

(e) The devices demonstrate only transferable mounting to the cap.

(f) The cap rear crown body is not conveniently foldable within the frontal crown body in a baseball cap style reinforcement structure (Hooser).

(g) The shaping structure may affect wearer comfort by adding unnecessary weight (Ford) or physically contacting the wearer (Stone, Hooser).

(h) The devices do not promote utilization of a reinforced cap crown to support exterior utility attachments mounted to the crown.

Eyewear of various types, especially sunglasses, are often worn together with a frontally billed cap, the cap bill shading the eyewear lenses, thereby reducing visual glare. The enhanced utility of wearing eyewear together with a billed cap has promted inventors to provide arrangements for attaching eyewear directly to a billed cap.

As the cap bill is normally the only structured portion of a soft cap, the bill would appear to be the logical part of the cap on which to mount eyewear. This approach has been taken by prior inventors, as exemplified by U.S. Pat. Nos. 4,726,074 to Baclit (1988), 4,541,125 to Phillips (1985), 4,304,005 to Danley (1981), and 2,725,560 to Feldman (1948).

The Baclit device involves a pivotal eyewear visor attachable to a cap bill with opposite side bill edge gripping jaws. The Phillips arrangement discloses a pair of underside bill clips joined to a central pivot mechanism carrying an eyewear. Danley discloses a hook and loop joining arrangement between a wire lens support and the underside of a cap bill. Feldman utilizes a set of channeled tracks secured to the underside of a cap bill for engaging swivels joined to an eyewear.

U.S. Pat. No. 857,838 to Shaw (1907), discloses an eyewear attached to the temple areas of a cap by utilizing swing arm links jointed to the forward temple bars.

While these devices relate utility as cap mounted eyewear in the configurations disclosed, they also demonstrate disadvantages associated with prior art in the field of cap mounted eyewear:

(i) The devices do not promote the utilization of a reinforced crown temple rim region of a soft cap to support crown mounted eyewear.

(j) The devices do not offer a cap supported eyewear which is vertically positionally adjustable relative to the eyes of the wearer.

(k) The devices do not provide a cap supported eyewear which offers peripheral eye protection.

(l) The devices do not offer a cap supported eyewear wherein the attitude at which the cap may be worn is independently selectable relative to the eyewear position (Baclit, Phillips, Danley, Feldman).

(m) The device requires that the cap supported eyewear rest on the nose of the wearer (Shaw).

(n) The device does not offer a cap supported eyewear which can be worn over conventional eyewear resting on the nose and ears (Shaw).

(o) The devices do not offer a cap supported eyewear which can be positioned to the rear of the cap, should the cap be worn backwards (Baclit, Phillips, Danley, Feldman).

(p) The devices do not offer a cap supported eyewear which can be located to a nonuse or stored position away from the underside of the cap bill or secured in a nonbill stored position if desired (Phillips, Danley, Feldman).

OBJECTS AND ADVANTAGES

Accordingly, several objects and advantages of the invention are:

(a) To provide a lightweight crown reinforcing structure for a soft cap which is simple and inexpensive to manufacture, utilizing primarily die-cut plastic sheet stock for the main reinforcing element.

(b) To provide a crown reinforcing structure which is installable and usable in a variety of modes and stages including:

a crown rim reinforcing structure functioning as a base;

an implement mounting adapter detachable from the base;

a detachable crown body shaping structure adjustable from the base;

a detachable flotation medium supported by the crown body shaping structure.

(c) To provide a crown reinforcing structure which may be utilized with a variety of cap styles.

(d) To provide a crown rim reinforcing structure which is installable either interiorly or exteriorly of the cap crown.

(e) To provide a crown rim reinforcing structure which is transferable to an existing cap or permanently attachable to a cap during or after manufacture.

(f) To provide a crown rim reinforcing structure in which the rear crown body is conveniently foldable within the frontal crown body across the reinforcing structure.

(g) To provide a cap crown reinforcing structure which is physically comfortable for the wearer.

(h) To provide a cap crown reinforcing structure which is adaptable to permit the cap to support a variety of utility attachments from the crown temple rim region.

(i) To provide eyewear which utilizes the reinforced character of the crown temple rim region of a soft cap, by adapting the eyewear to be supported from the crown temple rim region.

(j) To provide a crown supported eyewear which is vertically positionally adjustable relative to the eyes of the wearer.

(k) To provide a crown supported eyewear which offers peripheral eye protection.

(l) To provide a crown supported eyewear wherein the attitude at which the cap may be worn is independently selectable relative to the eyewear position.

(m) To provide a crown supported eyewear which does not necessarily rest on the nose of the wearer.

(n) To provide a crown supported eyewear which can be worn over conventional eyewear.

(o) To provide a crown supported eyewear which is positionable from the rear of the cap, should the cap be worn backwards.

(p) To provide a crown supported eyewear which is conveniently locatable to a nonuse or stored position out of the line of sight of the wearer and securable in the stored position if desired.

Further objects and advantages of the invention are to provide a crown reinforcing structure or crown supported eyewear which can be attached to a soft cap without physical alteration of the cap; to provide a crown mounted eyewear front which can be utilized for a variety of purposes, such as safety glasses, sunglasses or prescription lenses. Still further objects and advantages of the invention will become apparent from a consideration of the drawings and ensuing description.

DRAWING FIGURES

In the accompanying drawings like reference numerals are used to indicate like parts in the various views.

FIG. 1 is a perspective view partially broken away, showing a cap supplemented with interior cleat cards constructed according to one embodiment of the invention, the cleat cards being secured within the cap by integral foldable ears.

FIG. 2 is a fragmentary perspective view of one side of a cap showing an interior cleat card secured by a detachable clip.

FIG. 3 is a fragmentary perspective view of one side of a cap, showing an exterior cleat card secured by a sewn connection.

FIG. 4 is a perspective view partially broken away, of a cap showing interior cleat cards engaged to a support band.

FIG. 5 is a fragmentary perspective view, partially broken away, showing the relationship of a cap interior cleat with the cap headband, the cleat incorporating an integral clip portion.

FIG. 6 is a fragmentary perspective view of a cap interior cleat card which includes headed pins.

FIG. 7 is a perspective view partially broken away, of a detachable securing clip which incorporates a rotatable implement adapter.

FIG. 8 is a fragmentary perspective view, partially broken away, showing an interior cleat card secured by a detachable clip which incorporates a down turned lip to engage the cleat.

FIG. 9 is a fragmentary perspective view, partially broken away, showing the relationship of a cap interior cleat card with the cap headband, the cleat being secured by a detachable clip which incorporates a pin and hole connection and an implement engagement adapter in partially exploded detail.

FIG. 10 is a fragmentary perspective view, partially broken away, showing a clip to cleat engagement which incorporates a movable clasp.

FIG. 11 is a perspective view partially broken away, showing a detachable securing clip which incorporates a detachable implement engagement adapter.

FIG. 12 is a fragmentary perspective view, partially broken away, showing a cap interior cleat foldable ear secured by an overlying detachable clip.

FIG. 16 is a perspective view partially broken away, showing a cap interior cleat band secured by an exterior detachable clip.

FIG. 17 is a perspective view of the exterior detachable securing clip of FIG. 16.

FIG. 18 is a fragmentary perspective view, partially exploded, of a cap side showing a penlight mounted to the cap.

FIG. 19 is a fragmentary perspective view, partially broken away, showing an exterior cleat band restrained through the unbreached crown material by a detachable clip.

FIG. 20 is a perspective view of the detachable securing clip of FIG. 19.

FIG. 21 is a fragmentary perspective view of a cap side showing an exterior cleat band secured by a mechanical fastener, the band having a fold delineation, an integral implement adapter and a friction enhancing element.

FIG. 22 is a sectional view taken along line 22 of FIG. 21.

FIG. 23 is a perspective view of a cap with cantilevered eyewear adapted for use with the invention.

FIG. 24 is a fragmentary perspective view of conventional eyewear with an adapter temple.

FIG. 25 is a fragmentary perspective view of an adapted eyewear and a fragmentary exploded detail of a temple bar pivotal connection.

FIG. 26 is a fragmentary perspective view of an adapted eyewear.

FIG. 27 is a fragmentary perspective view of conventional wire frame eyewear with a temple adapter piece.

FIG. 28 is a fragmentary perspective view of conventional eyewear equipped with an adapter piece, the adapter piece shown in partially exploded detail.

DESCRIPTION AND OPERATION

Figure 13:
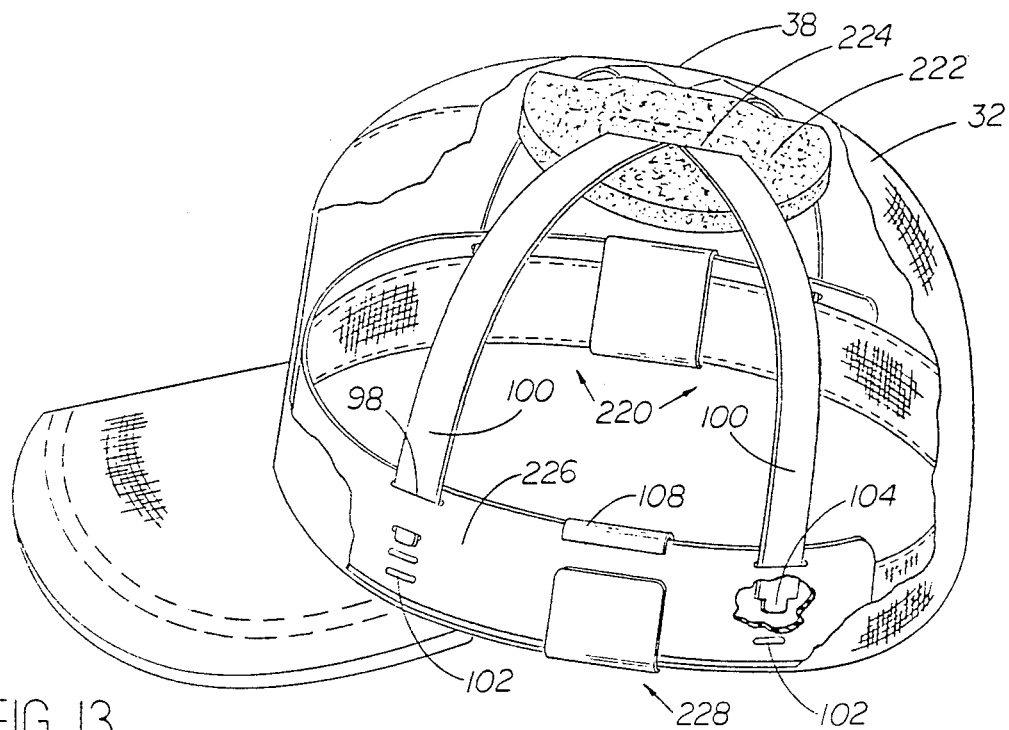
FIG. 13 is a perspective view partially broken away, showing a cap interior cleat band and a crown shaping device, the shaping device retaining a flotation medium.

Referring to the drawings in more detail and initially to FIG. 1, numeral 30 generally designates a soft baseball style or utility type cap having a hollow crown body 32 which is sized and shaped to fit the head.

The cap may be of a type that is commercially available and normally would not require alteration for use with the invention. The crown is typically soft, constructed from a lightweight flexible fabric which may be washed. The crown body 32 includes a frontal crown 34, a rear crown 36 and a top crown 38 portion. A relatively stiff frontal bill 40 joins a crown rim 42 to form a stiffened frontal radial corner 44. Extending continuous with the radial corner 44 are pliant crown temple rim 46 portions on opposite sides of the crown body.

As shown in FIG. 1, an interior headband 48 is typically joined to the crown rim 42 and radial corner 44. The upper edge 50 of headband 48 is normally free (not sewn to the cap crown 32), thus providing an interior open-top headband pocket 52. The pocket has a depth defined by the headband width and a bottom or seat 54 defined by the crown rim 42 and radial corner 44.

Although the drawing figures depict a cap crown having a continuous rim, this crown type is not specifically required for use with the invention. The cap crown can vary and may include a type having an interrupted rear rim size adjustment device.

In accordance with the invention a soft cap is supplemented with a reinforcing structure along the crown temple rim region 56. The structure has two primary elements, a cleat and a means for securing the cleat to the crown. The cleat and the securing means may be embodied in a variety of forms.

The principal function of the cleat is to provide structural reinforcement to the cap crown temple rim region 56 while extending the stiffened character of the radial corner 44 to the pliant crown temple rim 46.

The cleat may be installed either interiorly or exteriorly of the crown 32 and may take the form of a thin card, a card having an integral folding ear, a card having an integral clip portion, a card extended lengthwise to form a band or other configuration. An interior cleat may also function (though not necessarily) as a base for interior crown improvements which will be described.

The principal function of the securing means is to secure the cleat in a position adjacent the temple rim region of the cap crown. The securing means may allow the cleat to be transferable from cap to cap and may take the form of a foldable ear integral with the cleat FIG. 1, an integral clip FIGS. 5 and 14, or a detachable clip having numerous configurations. The securing means may also utilize substantially fixed methods of attachment between the cleat and the crown.

The securing means or cleat may also function (though not necessarily) to provide a base for mounting implements exteriorly of the crown from the temple rim region. The securing means or cleat may be adaptively modified to engage a light source, various forms of eyewear or other utility implements. The implement adapter may take numerous forms including those depicted in FIGS. 2-5, and 7-12, but the adapter form may be the configuration required to engage any selected implement.

As shown in FIG. 1, an interior cleat 58 may be embodied as a thin rectangular card 62 integrally joined with a double folding ear which functions to secure the location of the card. Card 62 is sized to be hand installed within the cap headband pocket 52 with the lower lengthwise edge of the card partially adjacent the radial corner 44 and partially adjacent the crown temple rim 46. The width or height of the card is somewhat greater than the depth of the headband pocket 52, thus allowing an upper lengthwise edge 64 of the card to extend above the headband upper edge 50 when the card is seated within the pocket.

The integral folding ear of cleat 58 includes an interior ear panel 66 which is integral with card 62 and foldable along a first line 68. An exterior ear panel 70 is integral with interior panel 66 and is foldable along a second line 72 to engage the crown temple rim 46. The eared cleat 58 may be produced from a suitable material such as plastic, or plastic overlying a thin metal core, such that once a fold is made along lines 68 and 72, panels 66 and 70 will remain in securing position. Fold location along lines 68 and 72 may be delineated by a series of spaced holes 74 which offer a line of decreased resistance to folding. The exterior panel 70 may be provided with an implement engagement adapter (not shown) including an outwardly projecting internally threaded stud 76 as shown in FIG. 2, or a detachable type adapter as shown in FIG. 11.

As further illustrated in FIG. 12, a cleat 60, having an integral folding ear, may be secondarily secured by hand installing an overlying detachable clip 78. The clip may be formed from a lightweight durable material such as plastic. By overlying the folded ear with the closely fitting clip, the cleat ear panels 80 and 82 are compelled to grip the crown temple rim region 56, thus enhancing resistance to cleat movement along the crown temple rim 46. A set of pins 84, projecting from an interior plate 86 of the clip body, engage paired holes 88 aligned through the cleat ear interior panel 80 and a card 90. The interior clip plate 86 joins an exterior plate 92 through a U-shaped bight section 94 which is sized to hold the crown temple rim 46. Methods other than the pin and hole arrangement depicted may be used to connect an overlying clip to a cleat having a foldable securing ear.

A cleat may be embodied as a thin card as shown in FIGS. 2, 3, 4, 8 and 9. The cleat card may be rectangular in shape with rounded corners and may be produced by die-cutting a suitable lightweight durable material such as plastic sheet stock. As illustrated in FIG. 2, an interior cleat card 96 may be provided with a receiving slot 98 or slots adjacent the upper edge of the card. The slot may function to receive a substantially perpendicular crown shaping strip 100 as shown in FIG. 13. A series of vertically spaced tab slots 102 may be provided to receive an end tab 104 of the shaping strip. It should be noted that the receiving slots 98 and spaced tab slots 102 may be incorporated with any interior cleat embodiment.

Cleat card 96, FIG. 2, may be secured by a detachable clip 106 which includes a bight lip 108 to connect with the cleat card and bight section 94 to hold the crown temple rim 46. An implement adapter, including stud 76, may be integrally joined to an exterior clip plate 110. As further illustrated in FIGS. 7 and 8, detachable securing clips utilizing bight lip 108 for connection to a cleat may be modified in various ways.

A detachable clip 112, FIG. 7, utilizing bight lip 108, includes an interior plate 114 joined to an exterior plate 116 through bight section 94. A rotatable threaded stud 118 projects through the exterior plate 116. Stud 118 includes a flanged base 120 and a crosswise opening 122. Opening 122 is adjacent and parallel with the face of clip plate 116. An implement appendage, including an eyewear temple bar 124 (FIG. 25), may be passed through opening 122 and secured against movement by an annular rim 126 of a threaded clamping cap (similar to that shown in FIG. 9) tightened on stud 118.

A detachable clip 128, FIG. 8, utilizing bight lip 108, includes an interior plate 130 joined to an exterior plate 132 through bight section 94. An adapter plate 134 integrally extends from the interior plate and may include stud 76.

FIG. 3 illustrates an exterior cleat card arrangement. A rectangular cleat card 136 may be attached to the crown temple rim region 56 by a sewn connection 138 or an adherent connection between the adjacent faces of the card and the crown material. The adherent connection may include an adhesive compound or a hook and loop fastener system. A series of vertically spaced holes 140 define a fold delineation across the cleat. The fold delineation offers a line of decreased resistance to folding should the rear crown body 36 be folded into the frontal crown 34. An opening through the cleat in the form of a T-slot 142 may function as an implement adapter.

An interior cleat card 144, FIG. 4, may include vertical slots 146 at the opposite ends of the card. The slots function to receive a support band 148. The support band can provide increased structural reinforcement along the crown temple rim 46, and the cleat card 144 or cards can adjust along the band within the headband pocket 52. The cleat cards 144 may be secured by a detachable clip 150. An exterior clip plate 152 may include an implement adapter having a slot 154. The slot retains a flanged 156 which may traverse within the slot. Clip 150 may be connected to card 144 by the use of a movable clasp 158.

As shown with greater detail in FIG. 10, clasp 158 has parallel side plates 160 separated by a pair of cross pins 162. A detachable clip 164 includes an interior plate 166 having paired holes 168. Each hole is sized and located to receive a cross pin 162 through a tapered guide slot 170. An expansion slit 172 allows the clip interior plate 166 to deform as a cross pin passes through the guide slot 170. As pins 162 engage holes 168, outside plate 160 clasps the upper edge of a cleat 174, thus connecting the clip to the cleat. Clip 164, or clips having an interior plate similar to plate 166 (FIG. 11), may engage a pair of headed pins 176 (FIG. 6) projecting from a cleat card 178. Pins 176 are sized and located to engage the clip interior plate holes 168 as described.

As illustrated in FIG. 5, an interior cleat 180 may be embodied as a rectangular card 182 which is hand installable within the headband pocket 52. An integral securing clip 184 functions to secure card 182. A clip interior plate 186 integrally joins card 182 to a clip exterior plate 188 through bight section 94 which holds the crown temple rim 46. Cleat 180 may be produced from a plastic material which can be sufficiently hand deformed along the clip bight section 94 to allow the clip exterior plate 188 to slip over and engage the crown temple rim 46. The clip exterior plate 188 may incorporate an implement adapter including an externally threaded stud 190.

FIG. 9 illustrates the use of a detachable clip 192 with a pin and hole clip to cleat connection. Pins 84, projecting from the clip interior plate 86, engage paired holes 88 through a cleat card 194. The clip interior plate 86 integrally joins exterior plate 92 through bight section 94 which holds the crown temple rim 46.

The implement adapter illustrated in FIG. 9 includes the integral internally threaded projecting stud 76. The stud may interact with an opening provided on various implements, including an open slot 196 (FIG. 18) through a mounting bracket lug 198, or a closed slot 200 (FIG. 23) through a modified eyewear temple bar 202. The implement adapter may also include a friction enhancing member joined to the exterior clip plate face as shown by a friction washer 204. A threaded clamping knob 206, which functions to secure the location or attitude of the various implements, may be tightened on stud 76.

FIG. 11 illustrates an implement adapter as a detachable platform 208. The platform has a configuration which allows the platform to be engaged or disengaged from an exterior clip plate 210 as required by the user. The platform may incorporate an implement adapter as an integral internally threaded projecting square stud 212, but the adapter form may be the configuration required to engage any selected implement. It should be understood that the implement adapters illustrated and described represent a few of many possible adapter configurations.

As shown in FIGS. 13–16, an interior cleat may be embodied as a cleat card which has been extended lengthwise to form a band. The band may be produced from a suitable lightweight flexible material such as plastic. The band can provide increased structural support to the flexible crown temple rim region 56.

The installation of a crown shaping device 220 within the cap crown 32 is also illustrated in FIG. 13. The shaping device may be produced by die-cutting a lightweight durable material such as plastic sheet stock. The shaping device utilizes an interior cleat of the invention as a base and may take the form of a number of substantially perpendicular shaping strips 100. The strips are joined to the cleat by passing through the receiving slots 98 located on the cleat body. The strips are provided with end tabs 104 which are sized to engage the vertically spaced tab slots 102 previously described.

The shaping strips have a length which allows each strip to curve adjacent the interior top crown 38 and extend to an opposing crown rim region. The effective length of each shaping strip may be adjusted to generate tension within the crown body 32 material by selection of the appropriate tab slot 102.

Additionally, as illustrated in FIG. 13, the shaping strip 100 may function to retain a flotation medium within the crown adjacent the top crown 38 portion.

The flotation medium may be produced by die-cutting a float disk 222 from a sheet of lightweight, flexible, buoyant material such as closed cell plastic foam. The float disk can provide buoyancy to the cap and any attached implement should the cap be lost into a body of water. The float disk 222 may include a pair of through-slits 224 (only one of which is visible in FIG. 13) which function to receive the shaping strip 100 or strips. As further illustrated in FIG. 13, a cleat band 226, with the attached shaping strips 100 and float disk 222, may be secured within the cap crown (though not necessarily) by a detachable securing clip 228 which includes bight lip 108 or other clip to cleat connection. The securing clip may also incorporate an implement adapter (not shown).

Figure 14:
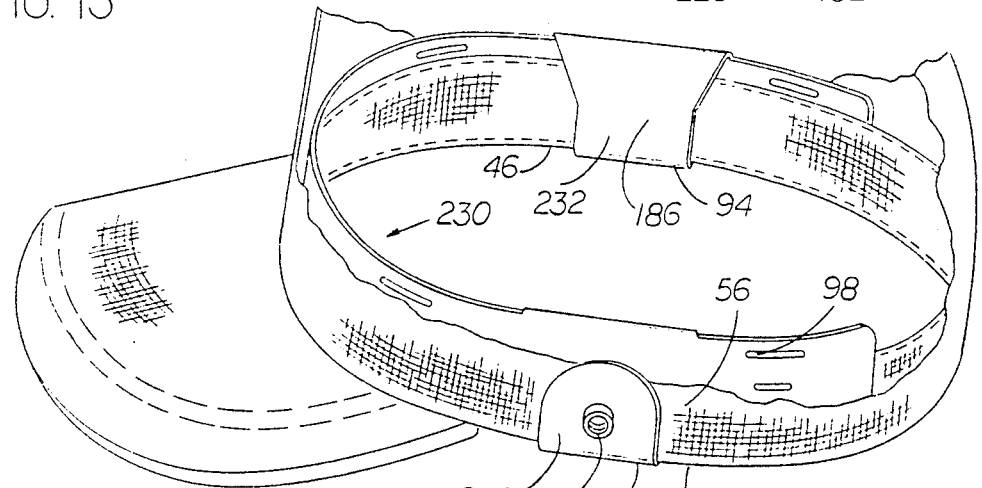
FIG. 14 is a fragmentary perspective view, partially broken away, showing a cap interior cleat band having integral securing clips.

As shown in FIG. 14, an interior cleat 230 may be embodied as a band having integral securing means in the form of foldable ears or clips 232. The length of the band between the clips allows each clip to locate along the crown temple rim region 56. As previously described, the clip interior plate 186 joins an exterior plate 234 through bight section 94 which holds the crown temple rim 46. Exterior plate 234 may incorporate an implement adapter, including stud 76.

Figure 15:
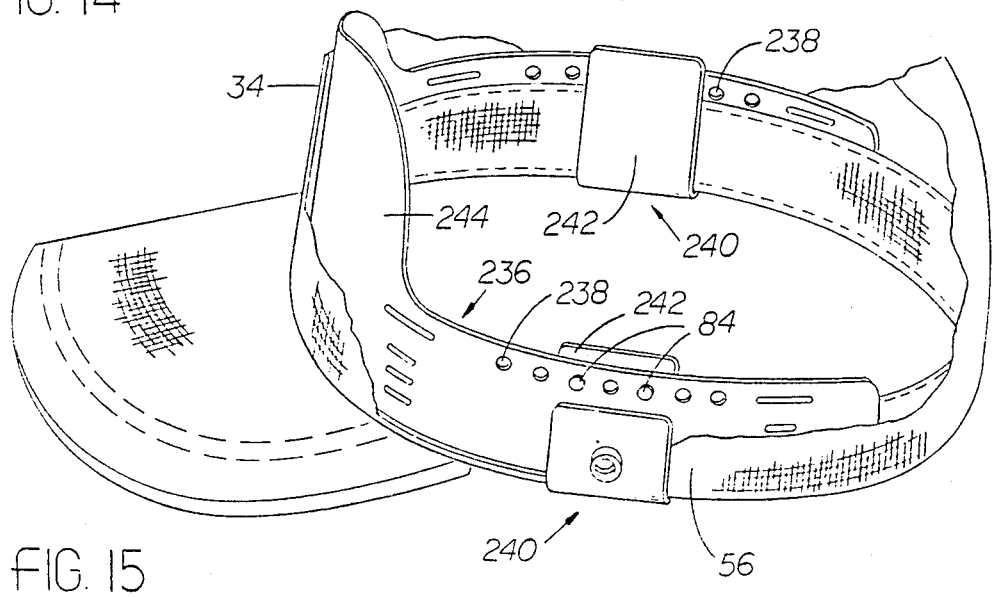
FIG. 15 is a fragmentary perspective view, partially broken away, showing a cap interior cleat band secured by a detachable clip.

FIG. 15 illustrates an alternative interior cleat band 236. The band includes a series of spaced holes 238 along those band portions which extend onto the temple rim regions of the crown. Spaced holes 238 receive pins 84 projecting from a detachable securing clip 240 interior plate 242. The wearer may selectively hand position clip 240 along the temple rim region 56 by moving the clip pins 84 from one set of spaced holes 238 to another set of holes. Band 236 may include a projecting flap 244. The flap provides interior backing to the cap frontal crown body 34, thereby enhancing the exterior shape and appearance of the frontal crown.

FIG. 16 illustrates the use of a detachable securing clip 246 which is shown with greater detail in FIG. 17. The clip includes an obliquely down turned bight lip 248 extending from the upper portion of an exterior plate 250. The exterior plate joins an interior plate 252 through bight section 94 which holds the crown temple rim 46. Bight lip 248 connects with the upper edge of an interior cleat band 254 through the unbreached crown material. The material adjusts to bight lip 248 by forming a small crease along the lip. The exterior connection to the cleat permitted by securing clip 246 will provide a relatively rigid base for any implement adapter which may be incorporated with the clip, including stud 76.

A penlight 256, FIG. 18, may be mounted to the securing clip 246 by utilizing the internally threaded projecting stud 76 as an integral implement adapter. Penlight 256 includes a tubular body 258 which typically functions as a battery compartment. The tubular body is formed at one end to retain a bulb 260 and at the opposing end to retain a switch 262. The penlight body may be gripped by a semicircular expandable sleeve 264 portion of a mounting bracket 266 lug 198. The lug presents the open slot 196 which is sized to receive the threaded projecting stud 76. The threaded clamping knob 206 may be hand tightened on stud 76, thus securing mounting bracket 266 to clip 246 and penlight 256 to the cap. The orientation or attitude of the penlight relative to the crown 32 may be selectively adjusted by loosening the clamping knob and redirecting the penlight as desired.

FIG. 19 depicts an exterior cleat band 270 which may be of particular use with a cap having a closed interior headband or caps having construction nonusable with interior cleats. Cleat band 270 may be installed exteriorly of the cap crown 32 with a lower lengthwise edge 272 of the band adjacent the radial corner 44 and extending coadjacent onto the opposite side crown temple rim regions 56. A detachable securing clip 274, FIG. 20, (only one of two is visible in FIG. 19) includes an obliquely down turned bight lip 276 extending from an interior clip plate 278. The interior plate joins an exterior plate 280 through bight section 94 which holds the crown temple rim 46. Bight lip 276 engages an upper edge 282 of cleat band 270 through the unbreached crown material from a position inside the crown. Securing clip 274 may incorporate an implement adapter, including stud 76.

FIG. 21 illustrates an exterior cleat band 284 which incorporates integral implement adapters as the internally threaded projecting stud 76 (only one of which is visible in FIG. 21). Cleat band 284 may be secured to the crown along the radial corner and extend onto the temple rim region 56 on opposite sides of the crown. The securing means may include a mechanical fastener as deformable rivets 286, best shown in FIG. 22. The rivets pass through cleat band 284 and the crown body material to the interior of the crown. The implement adapter may also include a friction washer 288 joined to the face of the cleat band and surrounding stud 76. The series of vertically spaced holes 140 may define a fold delineation across the cleat band. The fold delineation offers a line of decreased resistance to folding should the rear crown body 36 be folded into the frontal crow body 34.

As shown in FIG. 23, an eyewear 290 may be cantilevered from opposite sides of a cap crown by utilizing the exterior plates of cleat securing clips incorporated with an implement adapter. The cleat and securing means may preferably include the interior card 96 and detachable clip 106 illustrated in FIG. 2. The implement adapter may preferably include the internally threaded projecting stud 76, friction washer 204 and clamping knob 206 previously described and illustrated in FIG. 9.

Eyewear 290, FIG. 23, includes a lens front 292 presenting a nose opening 294 bounded by nose pads 296. The lens may be a safety type lens of a durable plastic material, a darkened or tinted type lens in order to serve as sunglasses or some other type of lens. The outer ends of the lens front 292 angle rearward and narrow into transition 298 portions which are integral with a pair of opposite side temple bars 202 (only one of which is visible in FIG. 23). Each temple bar 202 is provided with the elongated slot 200 which receives the internally threaded stud 76 (FIG. 9). A lightweight thrust washer 300 may be placed between the outside face of each temple bar 202 and the inside contacting rim 126 of each clamping knob 206 in order to distribute clamping force as the knobs are tightened.

Eyewear 290 can be adjusted forwardly and rearwardly relative to the eyes of a wearer by loosening knobs 206 and sliding the temple bars 202 forwardly or rearwardly, as permitted by the elongated shape of slots 200. In addition, with the knobs loosened, the eyewear front 292 can be pivoted upwardly and downwardly about the horizontal axis provided by opposite side projecting studs 76 (FIG. 9), thus allowing the eyewear front to be positioned as desired. Normally, the eyewear would be adjusted pivotally by the wearer until the nose pads no longer contact the nose, thus relieving all sensation of weight or pressure.

Additionally, with the clamping knobs 206 loosened, eyewear 290 may be located by the wearer to a nonuse or stored position away from the underside of the cap bill 40 (on top of bill 40 if desired) and secured in the selected location by retightening the clamping knobs.

As illustrated in FIGS. 23, 25 and 26, an eyewear front may include a forwardly projecting finger grasp 302. The finger grasp provides a convenient grasping point for adjusting the eyewear position prior to tightening the clamping knobs 206. Also, the thumb may be used to hold the finger grasp against the underside of the cap bill 40, thus immobilizing the eyewear while the cap is being put on or removed from the head of the wearer. The finger grasp may include a central hole 304 to enhance grip and provide a centered tactile reference when the grasp is being held between the fingers.

Alternative eyewear 306, FIG. 25, includes a lens front 308 with nose opening 294, nose pads 296 and the projecting finger grasp 302 previously described. The outer ends of the lens front angle rearward and narrow into transition 310 portions. On opposite sides of eyewear 306 temple bars 312 are provided, with each temple bar being connected at the forward end to the transition portion 310 by a pivot connection. As depicted in the exploded view of FIG. 25, a threaded fastener 314 extends through each lens transition 310, a friction washer 316 and the temple bar 124 or 312. A nut 318 is threaded onto each fastener 314 and tightened to secure the temple bar against pivotal movement relative to the lens transition 310. When nuts 318 are loosened, the lens front 308 may be pivoted about the axes of fasteners 314 to achieve the desired orientation.

The temple bars 312 of eyewear 306, FIG. 25, may be provided with an elongated slot 320. Each temple bar elongated slot 320 may additionally be provided with an access slit 322. The access slit will widen and permit the projecting member of an implement adapter, including stud 76 (FIG. 9), to slip through the slit into or out of the internal elongated slot 320 without the need to remove and then replace the clamping knob 206. It should be noted that the access slit 322 may be provided on other eyewear embodiments including, but not limited to, those illustrated by FIGS. 23, 24, 26 and 27. It should also be noted that eyewear temple bar engagement to an implement adapter does not necessarily require an elongated slot. The unslotted temple bar 124, depicted in FIG. 25, is securable with the implement adapter previously described and illustrated in FIG. 7.

Conventional eyewear may be provided with substitute adapter temple bars 324 as depicted in FIG. 24. Each temple bar 324 joins a conventional lens front 326 and frame 328 at a joint 330. The temple bar 324 may include an upwardly angling spatula type end 332 having the elongated slot 200 for receiving a projecting member of an implement adapter as previously described.

Conventional wire frame eyewear, FIG. 27, having a lens front 334, a frame 336 and temple bars 338 connected to the frame through a joint 340, may be provided with an adaptive end piece 342 for each temple bar. The end piece includes a spatula type terminal portion 344 having the elongated slot 200 and a hollow socket 346 to receive the temple bars.

Conventional eyewear temple bars may also be equipped with a slip on adapter piece 350 of the type shown in FIG. 28. A typical eyewear having a lens front 352, a frame 354 and temple bars 356 connected to the frame at a joint 358, may be fitted with the adapter by passing each temple bar through an adapter bight section 360. The bight section is formed by the opposing halves 362 of the adapter piece 350. The halves may be compressed to narrow bight section 360 and grip the temple bars 356, by tightening the mating nut 318 of a threaded fastener 364 which passes through the halves closely adjacent the bight section 360. The adapter piece may include an elongated slot 366 for receiving an implement adapter as previously described.

Another eyewear adapter 370 is shown in FIG. 26. The adapter includes opposite side temple bars 372 integrally joined to a front bar 374. The front bar may include the central forwardly projecting finger grasp 302. A lens front 376 and frame 378 may be joined to the front bar 374 by an expandable clasping sleeve 380 which permits pivotal movement of the lens front and frame. The frame 378 to front bar 374 connection may also utilize a threaded fastener or other attachment device. Each temple bar may include elongated slot 200 for receiving an implement adapter as previously described.

CONCLUSION, RAMIFICATIONS, AND SCOPE OF INVENTION

From the foregoing, it will be seen that the invention provides a unique, highly functional supplement to a soft baseball style or utility type cap. The reinforcing structure can be used with a variety of cap styles, and the implement adapter can have numerous configurations for engaging a variety of implements. Furthermore, the invention has additional advantages in that it provides a lightweight crown reinforcing structure for a soft cap which is simple and inexpensive to manufacture, utilizing primarily die-cut plastic sheet stock for the main reinforcing element.

it provides a crown reinforcing structure which is installable and usable in a variety of modes and stages.

it provides a crown rim reinforcing structure which is installable either interiorly or exteriorly of the cap crown.

it provides crown rim reinforcing structures which are transferable to an existing cap or permanently attachable to a cap during or after manufacture.

it provides a crown rim reinforcing structure in which the rear crown body is conveniently foldable into the frontal crown body across the reinforcing structure.

it provides a crown reinforcing structure which is physically comfortable for the wearer.

it provides eyewear which utilizes the reinforced character of the crown temple rim region of a soft cap, by adapting the eyewear to be supported from the crown temple rim region.

it provides a crown supported eyewear which is vertically positionally adjustable relative to the eyes of the wearer.

it provides a crown supported eyewear which offers peripheral eye protection.

it provides a crown supported eyewear wherein the attitude at which the cap may be worn is independently selectable relative to the eyewear position.

it provides a crown supported eyewear which does not necessarily rest on the nose of the wearer.

it provides a crown supported eyewear which can be worn over conventional eyewear.

it provides a crown supported eyewear which is positionable from the rear of the cap, should the cap be worn backwards.

it provides a crown supported eyewear which is conveniently locatable to a nonuse or stored position out of the line of sight of the wearer and securable in the stored position if desired.

While the above description contains many specificities, these should not be construed as limitations on the scope of the invention, but rather as an exemplification of several embodiments thereof. Other variations are possible. For example:

a cleat could be attached to the cap interior or exterior crown temple rim region, and a clip to join the cleat could be provided for specifically mounting exterior implements;

a cleat could embody a form to reinforce the crown temple rim regions of the cap and extend rearward to integrally provide the mating elements of a rear rim head size adjustment device;

a cleat could be joined to or integral with the internal stiffening element typically provided for the frontal cap bill;

a cleat could embody a form utilizing a plurality of securing clips on one side of the crown;

an interior cleat could be made integral with the crown shaping strip or strips;

a crown supported implement (for example eyewear) could be attached by a mating hook and loop fastener system between an inside face of the implement (temple bar) and an exterior face of a reinforcing cleat or the exterior surface of a securing clip or foldable ear etc.

It will be understood that certain features and subcombinations are of utility and may be employed without reference to other features and subcombinations.

Accordingly, the scope of the invention should be determined not by the embodiments illustrated, but by the appended claims and their legal equivalents.

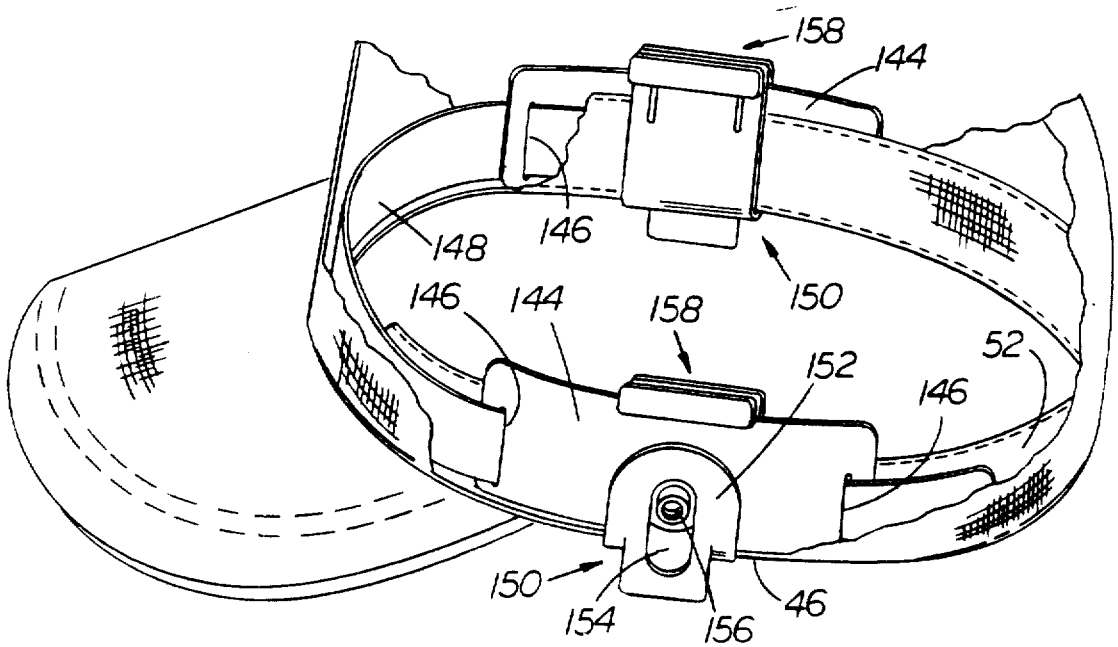

I claim:

1. A structure for reinforcing a cap of the type including a soft crown body of flexible material, said crown body having a pliant rim thereon, a frontal bill joined to the crown rim to form a stiffened radial corner, said structure comprising:
supplemental means for reinforcing said crown body;
means for restraining said supplemental means adjacent said crown body, the restraining means having means for holding said crown rim.

2. The structure of claim 1, wherein said restraining means includes connective means for joining said restraining means with said supplemental means.

3. The structure of claim 1, wherein said restraining means has size and shape to envelop a portion of said supplemental means.

4. The structure of claim 1, wherein said restraining means has size and shape to envelope a portion of said crown rim.

5. The structure of claim 1, wherein said restraining means comprises a bright member.

6. The structure of claim 5, wherein said bright member has a substantially U-shaped section.

7. The structure of claim 5, wherein said bright member is formed by folding said structure.

8. The structure of claim 1, further including:
an implement;
means for adapting at least one element of said structure to support said implement therefrom.

9. A structure for reinforcing a cap of the type including a soft crown body of flexible material, said crown body having a pliant rim thereon, a frontal bill joined to the crown rim to form a stiffened radial corner, said structure comprising:
supplemental means for extending the stiffened character of said radial corner to said crown body;
means for restraining said supplemental means adjacent said crown body, the restraining means having means for allowing movement of said supplemental means along and generally parallel with said crown rim while restricting movement of said supplemental means normal to the plane of said crown rim.

10. The structure of claim 9, further including:
an implement;
means for adapting at least one element of said structure to support said implement therefrom.

11. A structure for reinforcing a cap of the type including a soft crown body of flexible material, said crown body having a pliant rim thereon, a frontal bill joined to the crown rim to form a stiffened radial corner, said structure comprising:
supplemental means positioned alongside the crown body material for providing reinforcement thereto;
securing means for said supplemental means contrapositioned along the corresponding reverse side of said crown body material, said securing means having means for engaging said supplemental means through the crown material wherein said crown material remains unbreached.

12. The structure of claim 11, further including:
an implement;
means for adapting at least one element of said structure to support said implement therefrom.

13. A structure for reinforcing a cap of the type including a soft crown body of flexible material, said crown body having a pliant rim thereon, a frontal bill joined to the crown rim to form a stiffened radial corner, said structure comprising:
supplemental means for reinforcing said crown body;
means for restraining said supplemental means adjacent said crown body, said restraining means having at least one mating hook and loop fastener joined to said supplemental means and the corresponding portion of said crown body.

14. The structure of claim 13, further including:
an implement;
means for adapting at least one element of said structure to support said implement therefrom.

15. A structure for reinforcing a cap of the type including a soft crown body of flexible material, the crown having a pliant rim thereon and a foldably pliable template rim region bilateral thereof, a frontal bill joined to the crown rim to form a stiffened radial corner, said structure comprising:
supplemental means for reinforcing at least one temple rim region, said supplemental means having at least one foldable delineation thereacross, said foldable delineation having means for offering decreased resistance to folding;
means for securing said supplemental means adjacent said crown body wherein said foldable delineation generally overlies said temple rim region substantially perpendicular to said crown rim, whereby the crown temple rim is held generally aligned with the plane of said radial corner and the stiffened character of said radial corner is extended to said temple rim region, and whereby the rear crown body may be folded within the frontal crown body across the temple rim regions, the latter remaining foldably pliable.

16. The structure of claim 15, wherein said foldable delineation comprises at least one opening in said supplemental means.

17. The structure of claim 15, further including:
an implement;
means for adapting at least one element of said structure to support said implement therefrom.

18. A structure for reinforcing a cap of the type including a soft crown body of flexible material, said crown body having a pliant rim thereon, the interior crown including a headband joined to the crown rim to provide a pocket, a frontal bill joined to said crown rim to form a stiffened radial corner, said structure comprising:
supplemental means at least portionally positioned within the headband pocket adjacent said crown body for providing reinforcement thereto;
strip means for extending from said supplemental means away from said crown rim and curving adjacent said interior crown to an opposing crown rim region;
means for adjusting the effective length of said strip means.

19. The structure of claim 18, further including buoyant means retained by said strip means for providing flotation to said cap.

20. The structure of claim 18, further including:
an implement;
means for adapting at least one element of said structure to support said implement therefrom.

21. A structure for mounting an implement from a cap of the type including a soft crown body of flexible material, said crown body having a pliant rim thereon, the interior crown including a headband joined to the crown rim to provide a pocket, a frontal bill joined to said crown rim to form a stiffened radial corner, said structure comprising:
supplemental means at least portionally positioned within the headband pocket for cleating said crown body;
means for extending from said supplemental means across said headband to emerge exterior of said crown body for providing a mounting appendage exterior thereof, said extending means having connective means for joining with said supplemental means;
means for adapting at least one element of said structure to support said implement therefrom.

22. The structure of claim 2 or 21, wherein said connective means comprises an integral connection.

23. A structure for mounting an implement from a cap of the type including a soft crown body of flexible material, said crown body having a pliant rim thereon, a frontal bill joined to the crown rim to form a stiffened radial corner, said structure comprising:
supplemental means for cleating said crown body;
means for restraining said supplemental means adjacent said crown body, said restraining means having means for utilizing said crown rim;
means for adapting at least one element of said structure to support said implement therefrom.

24. A structure for mounting an implement from a cap of the type including a soft crown body of flexible material, said crown body having a pliant rim thereon and a pliant temple rim region bilaterial thereof, a frontal bill joined to the crown rim to form a stiffened radial corner, said structure comprising:
supplemental means located wholly exterior of said crown body for extending the stiffened character of said radial corner to at least one temple rim region;
means for restraining said supplemental means adjacent said crown body;
means for adapting at least one element of said structure to support said implement therefrom.

25. A structure for mounting an implement from a cap including a soft crown body of flexible material, said crown body having a pliant rim thereon, the interior crown body including a headband joined to the crown rim, a frontal bill joined to said crown rim to form a stiffened radial corner, said structure comprising:
supplemental means for cleating said crown body in a manner leaving said crown body unmodified and unbreached;
means for restraining said supplemental means adjacent said crown body in a manner leaving said crown body unmodified and unbreached;
means for adapting at least one element of said structure to support said implement therefrom.

26. A structure for mounting an implement from a cap including a flexible crown body having a rim thereon and at least one cleat adjacent thereto, a frontal bill joined to the crown rim to form a stiffened radial corner, said structure comprising:
detachable means for providing a mounting appendage exterior of said crown, said detachable means having connective means for coengaging said cleat and said crown rim;
means for adapting at least one element of said structure to support said implement therefrom.

27. The structure of claim 2, 21 or 26, wherein said connective means comprises a bight lip.

28. The structure of claim 2, 21 or 26, wherein said connective means comprises at least one pin and mating opening.

29. The structure of claim 2, 21 or 26, wherein said connective means comprises at least one clasp.

30. The structure of claim 8, 10, 12, 14, 17, 20, 21, 23-26 inclusive, wherein said implement comprises means for cooperating with the sight of a wearer.

31. The structure of claim 8, 10, 12, 14, 17, 20, 21, 23-26, inclusive, wherein said adapting means comprises at least one unmodified element of said structure.

32. The structure of claim 8, 10, 12, 14, 17, 20, 21, 23-26, inclusive, wherein said adapting means comprises means for modifying at least one element of said structure.

33. A cap-eyewear structure comprising:
a cap including a soft crown body of flexible material, the crown having a pliant rim thereon, a frontal bill joined to the crown rim to form a stiffened radial corner;
eyewear means for cooperating with the sight of a wearer;
means for supporting said eyewear means to effect cantilevered support of said eyewear means only from said crown body.

34. The structure of claim 33 wherein said supporting means comprises at least one unmodified element of said structure.

35. The structure of claim 33 wherein said supporting means comprises means for modifying at least one element of said structure.

36. The structure of claim 33, wherein said supporting means includes means for adjusting the position of said eyewear means.

37. A structure for mounting an implement from a cap of the type including a soft crown body of flexible material, said crown body having a pliant rim thereon, a frontal bill joined to the crown rim to form a stiffened radial corner, said structure comprising:

supplemental means for cleating said crown body;

means for restraining said supplemental means adjacent said crown body;

means for adapting at least one element of said structure to support said implement therefrom, said adapting means having at least one threaded member.

38. The structure of claim 1, 9, 11, 13, 15, 18, 21, 23, 24, 25 or 37, wherein said supplemental means extends adjacent said radial corner.

39. The structure of claim 1, 9, 11, 13, 15, 23, 25 or 37, wherein the interior crown includes a headband joined to said crown rim to provide a pocket and said supplemental means is at least portionally positioned within the headband pocket.

* * * * *

UNITED STATES PATENT AND TRADEMARK OFFICE
CERTIFICATE OF CORRECTION

PATENT NO. : 5,052,054

DATED : October 1, 1991

INVENTOR(S) : Donald A. Birum

Page 1 of 2

It is certified that error appears in the above-identified patent and that said Letters Patent is hereby corrected as shown below:

The title page showing the illustrative figure should be deleted to be replaced with the attached title page.

Title page, line 15 of the Abstract, "with" should be --which--

Column 7, line 51, insert --stud-- between "flanged" and "156".

Column 10, line 31, "crow" should be --crown--.

Column 13, line 54, "envelope" should be --envelop--.

Column 13, lines 57, 58 and 60, "bright" should be --bight--.

Column 14, line 50, "template" should be --temple--.

Claim 30, after "inclusive" delete ",", insert --or 37,--.

Signed and Sealed this

Twenty-ninth Day of December, 1992

Attest:

DOUGLAS B. COMER

*Attesting Officer*  *Acting Commissioner of Patents and Trademarks*

United States Patent

Birum

[11] Patent Number: 5,052,054
[45] Date of Patent: Oct. 1, 1991

[54] CAP STRUCTURE WITH IMPLEMENT ADAPTER

[76] Inventor: Donald A. Birum, Rte. 1, Box 23, Clark, Mo. 65243

[21] Appl. No.: 459,467

[22] Filed: Jan. 2, 1990

[51] Int. Cl.⁵ ............................................. A61F 9/00
[52] U.S. Cl. ........................................ 2/10; 2/185 B; 2/185 C; 2/185 R; 2/199; 2/422
[58] Field of Search ............... 2/10, 13, 185 B, 185 C, 2/185 R, 196, 199, 209.1, 209.2, 422

[56] References Cited

U.S. PATENT DOCUMENTS

| | | | |
|---|---|---|---|
| 1,171,155 | 2/1916 | Tannenbaum | 2/185 R |
| 1,586,701 | 6/1926 | Reppa | 2/196 |
| 1,611,771 | 12/1926 | Nathan | 2/185 C |
| 1,715,201 | 5/1929 | Levin | 2/185 C |
| 1,957,356 | 5/1934 | Rosen | 2/185 C |
| 2,578,112 | 12/1951 | Vaughn | 2/185 R |
| 2,704,367 | 3/1955 | Gellman | 2/199 |
| 2,803,016 | 8/1957 | Stevens | 2/185 B |
| 2,822,549 | 2/1958 | Glass | 2/185 R |
| 4,551,857 | 11/1985 | Galvin | 2/185 R |
| 4,764,989 | 8/1988 | Bourgeois | 2/422 |

FOREIGN PATENT DOCUMENTS 2754837  6/1979  Fed. Rep. of Germany .......... 2/10
818615   9/1937  France ............................. 2/185 B Primary Examiner—Werner H. Schroeder
Assistant Examiner—Diana L. Biefeld

[57] ABSTRACT

A reinforcing structure for a soft cap (30) is provided as a thin cleat (96) positioned adjacent the flexible temple rim region (56) of the cap crown (32). The cleat is secured interior or exterior of the crown by various transferable or substantially permanent methods of attachment. A transferable securing arrangement includes a detachable clip (106) having a bight lip (108) for connecting with an edge of the cleat (96) and a U-shaped bight section (94) for engaging the crown temple rim (46). A portion of the clip body exterior of the crown may be adapted to support various utility implements including an eyewear (290) having adaptive temple members (202). An interior cleat may also function as a base for interior crown improvements including a crown shaping strip (100) or strips with curve adjacent the interior crown body and are adjustable for effective length. The shaping strip may additionally serve to retain a float disk (222) adjacent the interior crown (38). The float disk provides buoyancy to the cap and any attached implement should the cap be lost into a body of water.

39 Claims, 5 Drawing Sheets